United States Patent [19]

Livingston

[11] Patent Number: 6,077,712

[45] Date of Patent: Jun. 20, 2000

[54] SEMICONDUCTOR CHEMICAL SENSOR

[75] Inventor: Peter M. Livingston, Palos Verdes, Calif.

[73] Assignee: TRW Inc., Redondo Beach, Calif.

[21] Appl. No.: 08/984,322

[22] Filed: Dec. 3, 1997

[51] Int. Cl.$^7$ .................................................. G01N 27/26
[52] U.S. Cl. ........................ 436/91; 436/149; 436/153; 422/50; 422/83; 422/98
[58] Field of Search ............................ 436/91, 149, 153; 422/50, 83, 98

[56] References Cited

U.S. PATENT DOCUMENTS

| | | | |
|---|---|---|---|
| 3,428,892 | 2/1969 | Meinhard | 324/71 |
| 3,645,999 | 2/1972 | Byrd | 260/95.5 |
| 4,572,900 | 2/1986 | Wohltjen | 436/151 |
| 4,636,767 | 1/1987 | Barger et al. | 338/34 |
| 4,674,320 | 6/1987 | Hirschfeld | 73/23 |
| 4,759,210 | 7/1988 | Wohltjen | 73/23 |
| 4,900,817 | 2/1990 | Batzel et al. | 540/128 |
| 4,911,892 | 3/1990 | Grace et al. | 422/94 |
| 4,992,244 | 2/1991 | Grate | 422/98 |
| 5,079,595 | 1/1992 | Suzuki et al. | 357/8 |
| 5,280,183 | 1/1994 | Batzel et al. | 257/40 |

OTHER PUBLICATIONS

Brauman, John I., "Instrumentation," *Science* 254 (5028):9 (1991).

Heckl, Wolfgang M. et al., "Surface Acoustic Wave Sensor Response and Molecular Modeling Selective Binding of Nitrobenzene Derivatives to (Aminopropyl) triethoxysilane," *Analytical Chemistry* 62:32–37 (1990).

Hughes, R.C. et al., "Thin–film palladium and silver alloys and layers for metal–insulator–semiconductor sensors," *J. Appl. Phys.* 62(3):1074–1083 (1987).

Hughes, R.C. et al., "Chemical Microsensors," *Science* 254:74–80 (1991).

Rouhi, A. Maureen, "Biosensors Send Mixed Signals," *C&En* 41–45 (1997).

*Primary Examiner*—Jill Warden
*Assistant Examiner*—Kevin P. Cannell
*Attorney, Agent, or Firm*—Michael S. Yatsko

[57] ABSTRACT

A chemical sensor for detecting a chemical species in a gas comprises a detector element including a porous organic semiconductor comprised of a material on which the chemical species in the gas is adsorbed. The chemical sensor further comprises a power source for producing a bias voltage and a depletion region in the detector element. The chemical species percolates through the organic semiconductor and into the depletion region under the bias voltage, causing a change in the capacitance of the detector element. A light source irradiates the gas with light before entering the detector element. The light changes the chemical properties of the chemical species and enhances the adsorption selectivity of the organic semiconductor. The chemical sensor can determine both the presence and concentration of the chemical species in the gas based on the change in capacitance in the detector element. The chemical sensor can be provided in a portable unit suitable for field testing applications.

25 Claims, 4 Drawing Sheets

SEMICONDUCTOR CHEMICAL SENSOR

BACKGROUND

The present invention is directed to the field of chemical sensors and, more particularly, to a semiconductor chemical sensor.

Measurements of very small concentrations of chemicals are needed, for example, to protect persons from chemical agents in warfare, and from poisonous gases and chemicals in industrial settings. An ideal chemical sensor would be small, lightweight and highly chemical specific and sensitive. Some known sensors are small, but not very sensitive and chemical specific, while some other known chemical sensors are chemical specific and sensitive, but much too large for field use applications. Trained dogs meet the needs of being small, chemical-specific and sensitive. Trained dogs are not, however, suitable for detecting chemical agents and poisonous gases and chemicals.

Accordingly, there is a need for a chemical detector that is small and lightweight, and is highly chemical specific.

SUMMARY

The present invention provides a chemical sensor and a method for detecting a chemical species in a gas that satisfies the above-described needs. The chemical sensor comprises a detector element including a porous layer comprised of an organic semiconductor material. The organic semiconductor is a material on which the chemical species in the gas is adsorbed. The chemical sensor comprises a power source for producing a bias voltage in the detector element. The chemical species percolates through the organic semiconductor and into a depletion region in the organic semiconductor under the bias voltage. The adsorption and percolation of the chemical species causes a change in the capacitance of the detector element.

A light source is disposed to irradiate the gas with light before the gas enters the detector element. The wavelength of the light is selected to correspond to a selected molecular resonance of the chemical species. Consequently, the light changes the chemical properties of the chemical species. For example, the chemical property change can be free radical formation, excited complex formation or the formation of molecular fragments by bond breakage. As a result of the chemical property change, the adsorption selectivity of the chemical sensor is enhanced.

The chemical sensor comprises means for determining the presence of the chemical species in the gas based on the change in capacitance in the depletion region caused by percolation of the chemical species. The chemical sensor preferably further comprises means for determining the concentration of the chemical species in the gas also based on the capacitance change.

The organic semiconductor can comprise an organic semiconductor material deposited on an electrical insulator such as a polymer material. The organic semiconductor material can be, for example, a heterocyclic compound such as a heterocyclic phthalocyanine compound, or an aliphatic compound. The composition of the organic semiconductor can be selected to provide a high degree of adsorption specificity with respect to the chemical species contained in the gas. The light source enhances this selectivity.

The detector element comprises a metal electrode forming an interface with the organic semiconductor. The metal electrode can be porous, or alternately can be non-porous. The porous metal electrode enables gas flow through the entire detector element.

The chemical sensor can be provided in a portable, hand carried unit suitable for field testing applications. The portable chemical sensor can comprise a fan for drawing the gas into the detector element to enhance the rate of chemical detection.

The chemical sensor according to the present invention is small and lightweight, and can detect very low concentrations of specific chemicals at a high degree of chemical specificity.

DRAWINGS

These and other features, aspects and advantages of the present invention will become better understood from the following description, appended claims and accompanying drawings, in which:

DESCRIPTION

The present invention is a semiconductor chemical sensor for determining the presence and concentration of a chemical species in a gas. The gas can be an airborne sample tested at a site using a portable version of the semiconductor chemical sensor. The semiconductor chemical sensor can alternately be used at a testing laboratory, for example, and the gas can be a sample taken from a test site.

Figure 1:
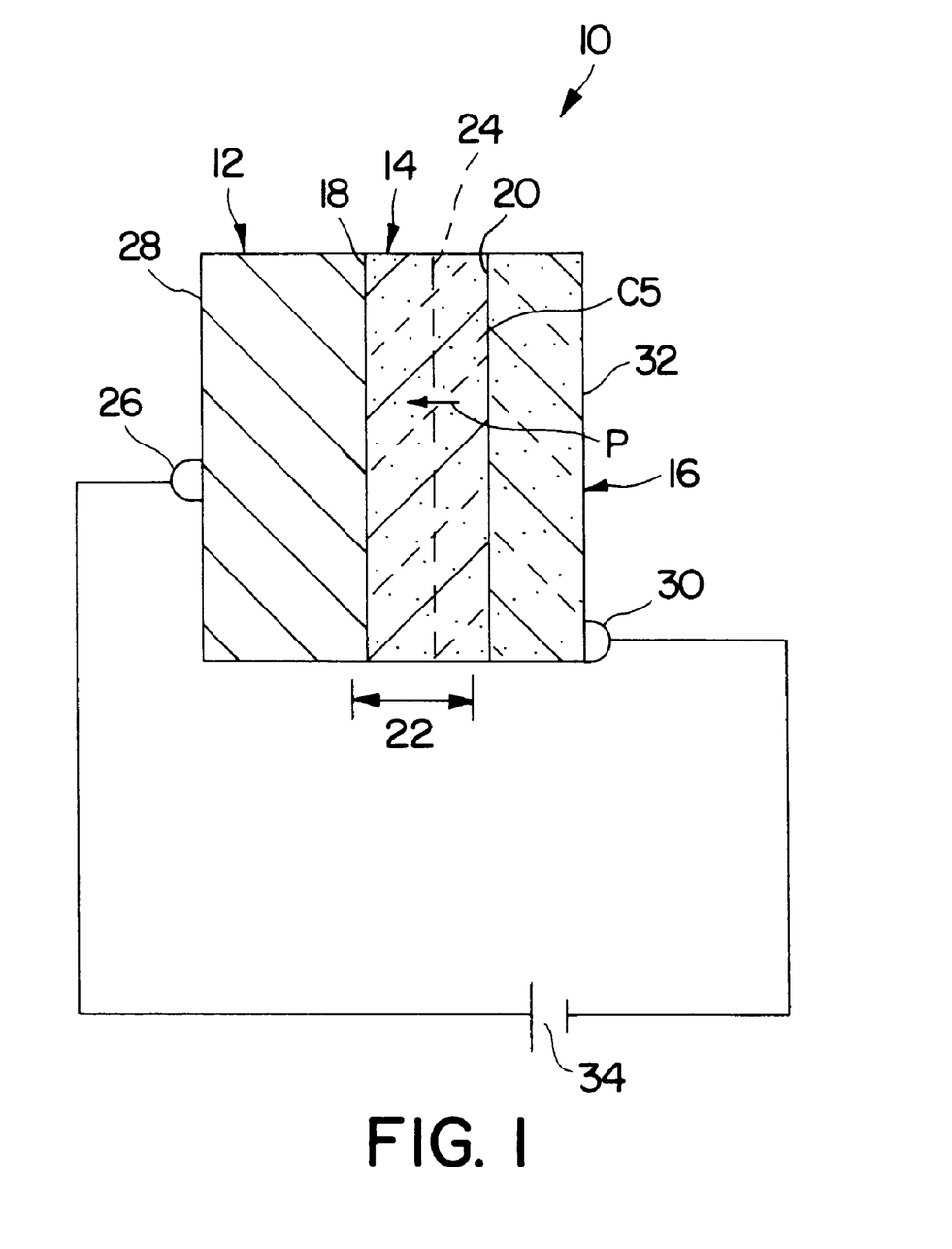
FIG. 1 is a sectional view of a detector element of a semiconductor chemical sensor according to the present invention.

FIG. 1 illustrates an embodiment of a detector element 10 of the semiconductor chemical sensor according to the present invention. The detector element 10 comprises a metal electrode 12, an organic semiconductor 14 adjacent to the metal electrode 12, and a porous electrode 16 adjacent to the organic semiconductor 14. The metal electrode 12 and the organic semiconductor 14 form a first interface 18 therebetween, and the organic semiconductor 14 and the porous electrode 16 form a second interface 20 therebetween.

A depletion region 22 sized approximately as shown is formed at the metal electrode 12 and the organic semiconductor 14. The depletion region 22 has dielectric properties such that the detector element 10 functions as a variable capacitor. The capacitance changes as a specific chemical species that binds to the organic semiconductor material percolates through the organic semiconductor 14 between the porous electrode 16 and the metal electrode 12. Other organic molecules are not adsorbed on the organic semiconductor material and, consequently, do not affect the capacitance. The front 24 of the chemical species moves through the organic semiconductor 14 as the chemical species percolates as depicted by arrow P. The chemical species is present in the organic semiconductor 14 in the region CS between the front 24 and the second interface 20.

An ohmic contact 26 is provided on an outer surface 28 of the metal electrode 12, and a ohmic contact 30 is provided on an outer inlet surface 32 of the porous electrode 16.

A power source 34 such as a battery is electrically connected to the ohmic contacts 26, 30. The power source 34 produces a bias voltage across the first interface 18 between the metal electrode 12 and the organic semiconductor 14.

The semiconductor chemical sensor measures the drift rate of the front 24 of the chemical species in the gas phase into the depletion region 22. The drift rate of the chemical species under bias voltage conditions across the depletion region 22 is determined by the rate of percolation of the chemical species through the organic semiconductor 14. The drift rate is chemical-specific, and the time rate of change of capacitance of the detector element 10 is, accordingly, also characteristic of a particular chemical species. The concentration of the chemical species in the gas sample can also be determined based on the change in the capacitance at the depletion region 22 caused by percolation of the chemical species. Accordingly, the chemical sensor can determine the presence and concentration of the chemical species in the gas sample.

The metal electrode 12 can be comprised of gold, silver, platinum or the like. The metal electrode 12 in the embodiment shown in FIG. 1 is non-porous so that the chemical species does not migrate through the metal electrode 12.

The organic semiconductor 14 is comprised of a porous material that has semiconducting properties. The composition of the organic semiconductor 14 is selected so that the chemical species of interest contained in the gas sample can be adsorbed on the organic semiconductor 14 and percolate at a chemical-specific rate. The chemical species can be an organic molecule or a fragment of an organic molecule as described in greater detail below. The organic semiconductor material chemically binds to the chemical species. Preferably, the organic semiconductor material is stereospecific with regard to the chemical species to achieve physical matching. By achieving such stereospecificity, the possibility that some other chemical species present in the gas that mimics the chemical species is absorbed on the organic semiconductor material is reduced, so as to reduce the possibility of false readings of the chemical species of interest being present in the gas by the chemical sensor.

The organic semiconductor 14 can be comprised of an organic heterocyclic compound having semiconducting properties. The band gap of these compounds is primarily determined by the pi-electron energy separation from the electrons localized around each carbon atom. The pi-electrons are relatively free to move throughout the organic molecule as compared to the carbon-bound electrons. Chemical binding to heterocyclic compounds is expected to be relatively weak, but highly chemical specific. Cyclic organic compounds can be attracted to the organic semiconductor through the attraction of the circulating pi-electrons where free-radicals can 'open up' some portion of the ring structure causing it to increase the conduction band gap. Consequently, many heterocyclic compounds are semiconductors.

A paper by G. R. Bird entitled "Organic Semiconductors: A Critical Test of Organic P-N-photovoltaic Cells," lists a number of heterocyclic phthalocyanines (dyes) that incorporate at least one metal atom, and perylenes containing no metal atoms, which generate current when exposed to light (photovoltaic effect). It is also envisioned that variants of the phthalocyanines with side chains can be prepared to promote hydrogen-bonding. Depending on the physical location of these side chains, chemical species bind more or less tightly depending on how closely they match or conform to the semiconductor binding sites.

Known aliphatic compounds also exhibit semiconducting and chemical-group specific adsorption properties. For example, (amino propyl)triethoxysilane can separate nitroanisole, nitrotoluene, 4-fluoronitrobenzene, nitrobenzene and acetone, among other compounds, based upon the variety and strength of the hydrogen bonding that is compound specific.

The porous electrode 16 can be comprised of an inorganic semiconductor material. To avoid the formation of a depletion region at the second interface 20 between the organic semiconductor 14 and the porous electrode 16, the porous electrode 16 can be a heavily doped ($n^+$) n-type material. For example, if the organic semiconductor 14 is an n-type material, the porous electrode 16 can be an etched grid structure comprised of silicon. The silicon can be heavily doped with a donor such as P, As, Sb or the like.

The porous electrode 16 allows the chemical species to readily migrate from the inlet surface 32 to the second interface 20. The pore size of the porous electrode 16 can be varied to enable passage of different sized organic molecules of interest. The pore size can be, for example, from about 10 $\mu$m to about 100 $\mu$m.

Figure 2:
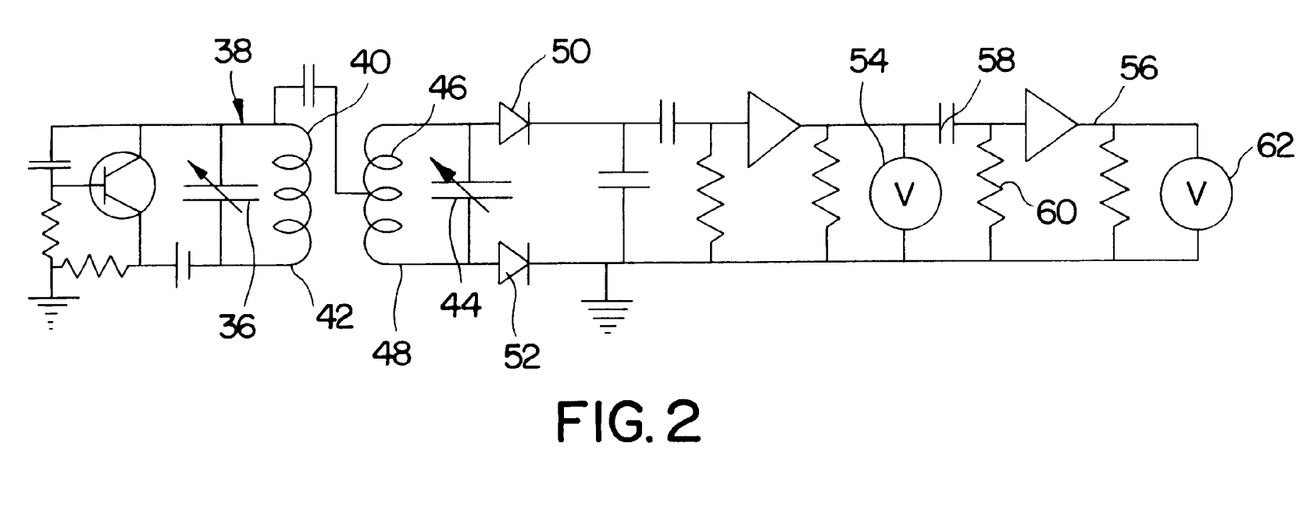
FIG. 2 is a circuit diagram of an electrical circuit for use in the semiconductor chemical sensor according to the present invention.

Referring to FIG. 2, the semiconductor chemical sensor comprises means for determining the time rate of change in capacitance at the first interface 18 under bias voltage conditions. This capacitance change can be related to the presence of a specific chemical species in the organic semiconductor 14. As shown, the detector element 10 is represented as a variable first capacitor 36 in a discriminator circuit 38. The capacitor 36 and a first inductor 40 in a first LC circuit 42 are connected to a variable second capacitor 44 and a second inductor 46 in a second LC circuit 48. The first capacitor 36 has a capacitance $C_1$ and the first inductor 40 has an inductance $L_1$. The resonant frequency $f_1$ of the first LC circuit 42 is given by: $f_1=(\frac{1}{2}\pi L_1 C_1)^{1/2}$. Similarly, the second capacitor 44 has a capacitance $C_2$ and the second inductor 46 has an inductance $L_2$, and the resonant frequency $f_2$ of the second LC circuit 48 is given by: $f_2=(\frac{1}{2}\pi L_2 C_2)^{1/2}$. The circuits 42, 48 can be tuned. As the chemical species percolates through the organic semiconductor 14 between the second interface 20 toward the first interface 18 (FIG. 1), the capacitance of the depletion region 22 changes such that $C_1$ changes by an amount $\Delta C_1$. This capacitance change causes the product of $L_2 C_2$ to become unbalanced with respect to the product $L_1(C_1+\Delta C_1)$. A pair of diodes 50, 52 are connected to the circuits 42, 48. The change in frequency due to the capacitance change $\Delta C_1$ causes the currents and associated voltages $V_1$, $V_2$ of the respective diodes 50, 52 to also become unbalanced by a difference of $|V_1-V_2|$. This difference can be measured using a calibrated center-null voltmeter 54. When steady-state is reached (such that the concentration of the chemical species between the inlet surface 32 and the front 24 is approximately constant), the frequency deviation stabilizes and the deflection of the voltmeter 54 from nominal conditions is proportional to the number of the chemical species in the depletion region 22. Using this deflection value and the volume of the gas sample containing the chemical species that enters into the detector element 10 during the time period over which the capacitance change occurs, the concentration of the chemical species in the gas sample can be determined.

The semiconductor chemical sensor preferably also comprises means to classify the compound type of the chemical species based on the capacitance change. The identity of the chemical species can be determined by differentiating the voltage difference $|V_1-V_2|$ with an RC time constant using an output differentiator circuit 56, including a resistor 58, a capacitor 60 and a voltmeter 62. The slope of the resulting curve, $|V_1-V_2|/\Delta t$, can be used to determine the presence of the chemical species, by comparing the slope to predetermined data generated for the chemical species during calibration of the semiconductor chemical sensor. Different chemical species for which data is available can be identified based on the slope generated during actual detection.

Figure 3:
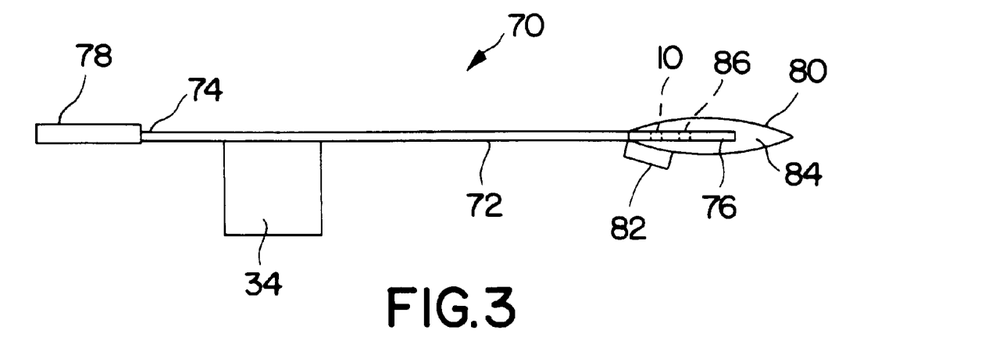
FIG. 3 illustrates a portable version of the semiconductor chemical sensor device according to the present invention.

As illustrated in FIG. 3, the semiconductor chemical sensor can be a portable, hand-held chemical sensor device 70 suitable for field testing applications. The chemical sensor device 70 can comprise an elongated support member such as a rod 72 having opposed ends 74, 76. A handle 78 can be provided at the end 74 for grasping by a user. The detector element 10 and other circuitry of the semiconductor chemical sensor can be disposed at the end 76 of the rod 72. The circuit illustrated in FIG. 2 can be fitted in a standard transistor container. A cover 80 such as a shroud can partially surround the detector element 10. An aspirating fan 82 is typically disposed to draw the surrounding atmosphere into the space 84 inside the cover 80 to enhance the rate of detection. The operation of the fan 82 can be calibrated such that a known volumetric flow rate of the gas sample is drawn into the detector element 10. Accordingly, the concentration of the chemical species in the gas sample can be determined, based on the voltage difference $|V_1-V_2|$, the volumetric flow rate of the gas, and the time duration of sampling.

A device that provides a readout of the test results can be included in the chemical sensor device 70 (not shown).

As described above, the chemical selectivity of the semiconductor chemical sensor depends on the chemically-unique percolation rate of specific chemical species through the organic semiconductor. To enhance the chemical selectivity by producing more selective adsorption of the chemical species on the organic semiconductor 14, and to reduce background signals, the chemical sensor device 70 preferably comprises a light source 86 disposed to irradiate the gas sample with photons before the gas sample enters the detector element through the inlet surface 32 of the porous electrode 16. The wavelength (or wavelengths) of the light is selected to correspond to a specific molecular resonance so as to cause some change in the chemical properties of the chemical species. The property change can be detected by the semiconductor chemical sensor. For example, the chemical change can be the formation of molecular fragments by breaking bonds in the chemical species, free radical formation, pi-electron activation or excited complex formation. The molecular fragments, free radicals and excited complexes can be detected by the chemical sensor. The enhanced adsorption selectivity can enable the chemical sensor to detect chemical species that may not otherwise be detectable without irradiating the chemical species. The light can also enhance the detection of a chemical species that is otherwise detectable, but at a lower level of chemical specificity. The use of light can enable lower levels of a given chemical species to be detected by the chemical sensor, by causing a higher capacitance change in the chemical sensor for a given amount of the chemical species in the gas sample, thus enhancing the certainty and accuracy of detection of the chemical species. By synchronizing the chemical species detection process with the light pulse, a highly chemical-specific, sensitive chemical detection can be achieved.

For example, the gas sample can be irradiated with visible or near-ultraviolet light from a light source such as a laser diode, immediately before the gas sample enters the detector element 10. The light source can be used in portable and non-portable versions of the chemical sensor.

The capacitance of the depletion region 22 in the detector element 10 changes as the chemical species percolates through the organic semiconductor 14 between the second interface 20 and the first interface 18. The semiconductor chemical sensor can saturate once the front 24 of the chemical species reaches the first interface 18 and the capacitance change stops. Reversing the voltage bias or heating the semiconductor chemical sensor with a light pulse can remove the saturation and enable continued operation.

Figure 4:
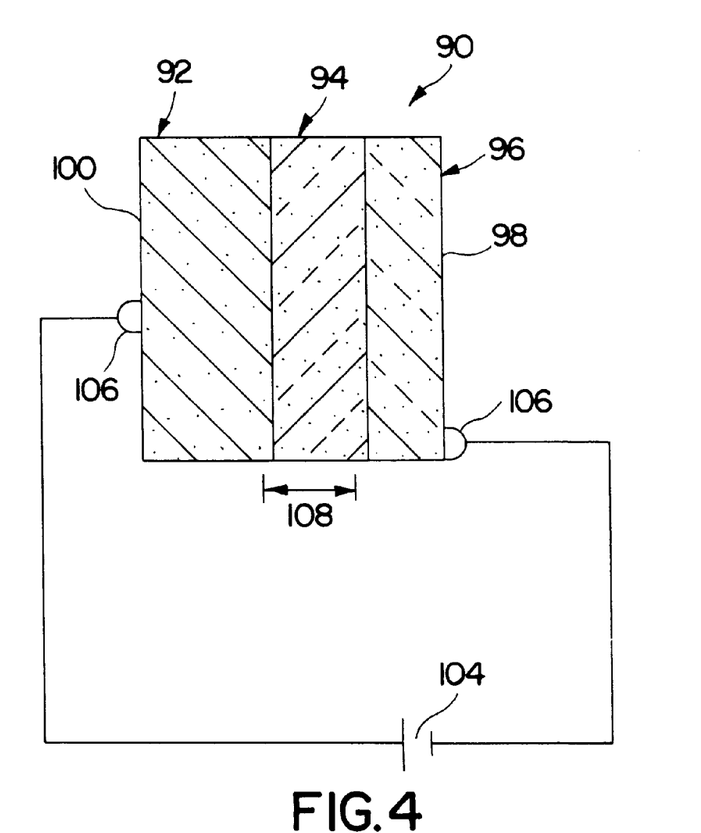
FIG. 4 is a sectional view of an alternate embodiment of the detector element of the semiconductor chemical sensor according to the present invention.

FIG. 4 illustrates an alternate embodiment of the detector element of the semiconductor chemical sensor according to the present invention. The detector element 90 comprises a porous metal electrode 92, an intermediate layer 94 and a porous inorganic semiconductor electrode 96. The porous metal electrode 92 allows gas flow through the semiconductor chemical sensor between the inlet surface 98 of the inorganic semiconductor electrode 96 and the outlet surface 100 of the porous metal electrode 92, such that the chemical sensor is a flowing gas sensor. The detector element 90 also comprises a power source 104 for producing a bias voltage, and ohmic contacts 106 to provide electrical contact.

The organic semiconductor 14 of the detector element 10 semiconductor chemical sensor of FIG. 1 can be replaced by the intermediate layer 94 comprising a substrate such as a neutral insulating mesh substance, and an organic semiconductor material such as a heterocyclic compound deposited on the mesh substance. The mesh substance provides insulating properties and has a composition that can bind to the organic semiconductor material. For example, the mesh substance can be nylon and other like polymeric materials. The mesh substrate also increases the strength of the intermediate layer 94.

The metal mesh electrode 92 and the mesh electrode 96 can have the same composition as in the detector element 10.

A depletion region 108 is formed in the intermediate layer 94 between the porous metal electrode 92 and the inorganic semiconductor electrode 96. The electrical capacity of the detector element 90 changes with time as the chemical species is absorbed on the organic semiconductor in the intermediate layer 94, causing it to become a better or poorer semiconductor, and, consequently changing the capacitance of the detector element 90.

The use of a light source to promote a photoactivation mechanism is advantageous in this embodiment. Light wavelengths can be selected to break certain bonds in the organic molecule to produce molecular fragments that can be detected by the semiconductor chemical sensor.

Figure 5:
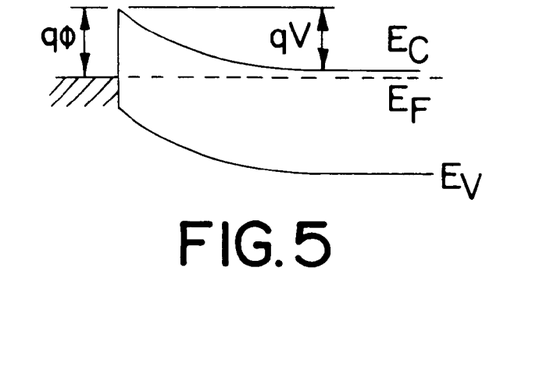
FIG. 5 is an energy band diagram of a typical metal-semiconductor junction at zero bias voltage conditions.

The physical basis for the operation of the present invention can be described as follows. FIG. 5 shows a typical depletion zone between a metal and a semiconductor under zero applied voltage conditions. $q\phi_m$ is the metal work function; $E_C$, $E_F$, and $E_V$ are the energies at the bottom of the conduction band, the Fermi level, and the top of the valence band, respectively; $qV_{mC}$ is the energy difference between the metal work function and the bottom of the conduction band energy. The depletion region thickness is essentially the distance between the metal and the distance at which $E_C$ approaches a constant.

Figure 6:
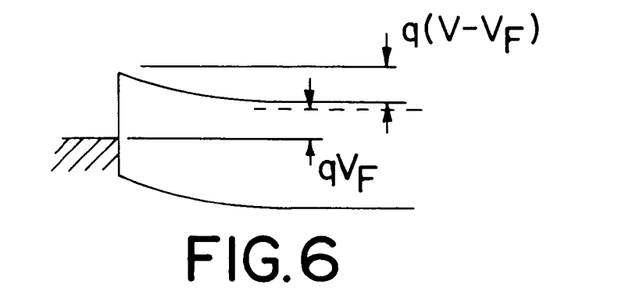
FIG. 6 shows the energy band diagram of FIG. 4 under forward bias conditions.
Figure 7:
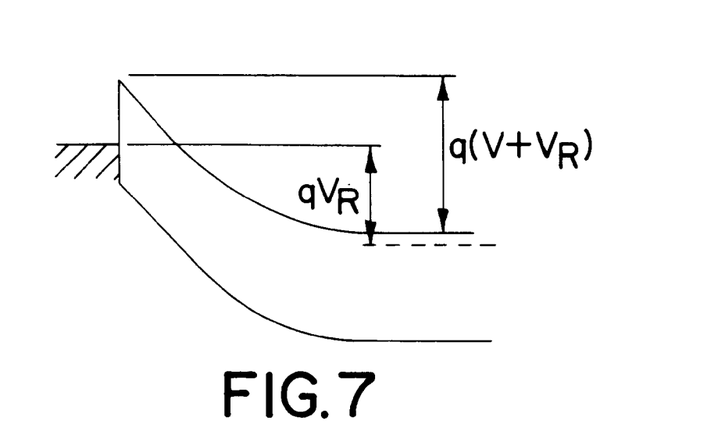
FIG. 7 shows the energy band diagram of FIG. 4 under reverse bias conditions.

FIGS. 6 and 7, respectively, illustrate the relationship of these energies under forward ($V_F$) and reverse ($V_R$) bias conditions.

In a semiconductor placed in contact with a metal electrode, hole and electron populations adjust themselves in the vicinity of the boundary to maintain overall charge neutrality. A depletion region having a width W is formed at the interface between the metal electrode and the semiconductor:

$$W = [2\epsilon'_S(V_{mC} - V - kT/q)/qN_D]^{1/2} \quad (1)$$

where $\epsilon'_S = \epsilon_S \cdot \epsilon_O$ is the relative dielectric permittivity of the semi-conductor medium ($\epsilon'_S \cong 12$ for Si, for example); $V_{mC}$ is the energy difference (volts) between the metal work function and the energy at the bottom of the conduction band in the semiconductor; V is an applied bias voltage; q is the charge; kT/q is the thermal energy; $N_D$ is the total donor concentration (molecules/volume); and $_O$ is the vacuum dielectric constant. A typical depletion layer thickness is about $10^{-4}$ cm.

If the semiconductor capacitance is primarily determined by the semiconductor depletion layer, then $C = \epsilon_S/W$ and an oscillator with a fixed inductor L resonates at a frequency f:

$$f = \sim 2^{1/2}(V_{mC} - V - kT/q)^{1/2})]/[4\pi^2 AL(qN_D\epsilon'_S)^{1/2}]^{1/2} \quad (2)$$

where A is the effective area of the capacitor. The frequency shift in terms of the effective dielectric permittivity is given by:

$$4\delta f/f = -\delta\epsilon_S/\epsilon_S \quad (3)$$

A variation in this quantity can be expressed as a variation in the number density of the chemical species using the Clausius-Mosetti equation which assumes additivity of the individual polarizations:

$$[(\epsilon'_S/\epsilon_O) - 1]/[(\epsilon'_S/\epsilon_O) + 2] = (4\pi/3)(\alpha_O n_O + \alpha_1 n_1) \quad (4)$$

where α expresses the molecular polarizability; the factor 3 in the denominator arises from the assumed isotropicity of the molecules and the subscripts 0, 1 refer to the detector medium before and with the chemical species, respectively. A first order variation in ε follows from Equation 4 in which $n_1$ is replaced by δn:

$$\delta\epsilon'_S \cong (4\pi/9\epsilon_O)(\epsilon'_S + 2\epsilon_O)^2 {}_1\delta n = (4\pi/9\epsilon_O)(\epsilon'_S + \epsilon_O)^2 {}_1(\Delta n/d \cdot A) \quad (5)$$

In the second equality, δ is replaced by the addition of the chemical species number, Δn, divided by the product of the drift distance, d, into the depletion layer and the capacitor effective area, A. The induced polarizability of the chemical species causes it to drift into the depletion region under the influence of the bias voltage. In a time δt, an amount n of the chemical species drifts into the depletion region:

$$\Delta n = Kn_i A\mu(V/W)\delta t \quad (6)$$

where K is a surface distribution coefficient, describing the take-up of the chemical species, and $n_i$ is the equilibrium concentration of the chemical species at the input surface of the detector element, A is the effective detector element area, and μ is the mobility of the chemical species as it percolates through the porous semiconductor.

According to Equation 6, as K increases, then Δn/St increases also. This increase relates to an increase in the drift rate of the chemical species through the semiconductor, and also an increase in the rate of capacitance change in the detector element.

Combining Equations 3, 5, and 6, the oscillator frequency changes exponentially with time:

$$\delta f/f = \delta t/\tau; \quad \tau = 9\epsilon_S(W^2/\pi(\epsilon_S + 2)^2\alpha_1(Kn_i) \cdot \mu \cdot V) \quad (7)$$

Equations 6 and 7 are approximations and do not take into account reverse percolation of the chemical species which depends on the chemical species concentration as well as other factors that determine steady state conditions. The steady state frequency offset can be regarded as being empirical and can be determined experimentally. Equation 7 is useful because it relates the rate of frequency change and properties of the chemical species; namely the product of the mobility, polarizability, and the concentration of the chemical species in the gas sample for a fixed bias voltage.

As an example, the chemical sensor can be used to test for the presence of cocaine in a gas sample. Using a portable version of the chemical sensor such as the chemical sensor 70, the gas can be drawn into the detector element (10 or 90) at a known flow rate using a calibrated aspirating fan. The gas sample can be irradiated with light at a wavelength effective to cause bond scission between the benzoyl ($C_6H_5CO$) and ecgonine ($C_9H_{15}NO_2$) groups. The wavelength can be about 6.69 μm. Other wavelengths can also be used to cause other changes in the chemical properties of the cocaine molecule. For example, the range 6.87–6.62 μm. The semiconductor phthalocyanine molecule can be synthesized to include hydrogen-bonding side-chains that preferentially attach the cocaine fragment, but that reject other species that do not have a conformal geometry. As the cocaine molecule or fragment percolates through the organic semiconductor, the capacitance in the detector element changes, and the rate of change and the magnitude of the change can be correlated respectively with the presence and concentration of the cocaine molecule in the gas, based on the measurements produced by the electrical circuitry such as shown in FIG. 2, in accordance with equation (7) described above.

The semiconductor chemical sensor according to the present invention can be used to detect suspected chemical species in gases in a wide range of applications. For example, the semiconductor chemical sensor can be used for: environmental monitoring of toxic chemicals such as trichloroethylene in air, soil and ground water; determining the status of equipment such as transformers, turbines and airplanes; internal combustion engine exhaust analysis of $O_2$, $NO_2$ and hydrocarbons; locating illegal drugs, explosives, and drug-manufacturing at portals in airports and by portable monitoring; inexpensive sensors for home hazards such as CO and natural gas; critical monitoring of chemical processes, including material separation, manufacturing and waste stream control; in vivo sensing of chemical concentrations of ions, pH, $pO_2$, $pCO_2$, glucose and the like; and research on complex chemical reactions.

Although the present invention has been described in considerable detail with reference to certain preferred versions thereof, other versions are possible. Therefore, the scope of the appended claims should not be limited to the description of the preferred versions contained herein.

What is claimed is:

1. A semiconductor chemical sensor for detecting a chemical species in a gas, comprising:
   a) a detector element comprising:
      i) an inlet surface; and
      ii) a porous layer comprised of an organic semiconductor material on which the chemical species is adsorbed, the porous layer having a depletion region;
   b) a power source electrically connected to the detector element to produce a bias voltage in the detector element such that the chemical species percolates through the porous layer and into the depletion region under the bias voltage, thereby changing the capacitance of the detector element;

c) a light source disposed to irradiate the gas with light before the gas enters the detector element at the inlet surface, the light source emits at least one light wavelength effective to change the chemical properties of the chemical species so as to enhance the adsorption selectivity of the organic semiconductor material with respect to the chemical, species; and d) means for determining the presence of the chemical species in the gas based on the change in capacitance in the depletion region.

2. The semiconductor chemical sensor of claim 1, wherein the detector element comprises:

i) a metal electrode forming a first interface with the porous layer; and ii) a porous electrode comprised of an inorganic semiconductor material forming a second interface with the porous layer, the porous electrode including the inlet surface.

3. The semiconductor chemical sensor of claim 1, further comprising means for determining the concentration of the chemical species in the gas based on the change in capacitance in the depletion region.

4. The semiconductor chemical sensor of claim 1, wherein the organic material is an n-type material and the mesh electrode comprises a heavily doped n-type silicon material.

5. The semiconductor chemical sensor of claim 1, further comprising means for drawing the gas into the detector element through the inlet surface.

6. The semiconductor chemical sensor of claim 1, wherein the light source comprises a laser diode.

7. The semiconductor chemical sensor of claim 2, wherein the metal electrode is non-porous.

8. The semiconductor chemical sensor of claim 2, wherein the metal electrode is porous.

9. The semiconductor chemical sensor of claim 1, wherein the porous layer comprises the organic semiconductor material on a porous insulating substrate.

10. The semiconductor chemical sensor of claim 1, wherein the organic semiconductor material comprises a heterocyclic compound.

11. The semiconductor chemical sensor of claim 1, wherein the organic semiconductor material comprises an aliphatic compound.

12. A semiconductor chemical sensor for detecting a chemical species in a gas, comprising:

a) a detector element including:
i) a porous metal electrode;
ii) a porous layer forming a first interface with the metal electrode, the porous layer being comprised of an organic semiconductor material on which the chemical species is adsorbed; and
iii) a porous mesh electrode forming a second interface with the intermediate layer, the mesh electrode having an inlet surface;

b) a power source for producing a bias voltage in the detector element, such that the chemical species percolates through the organic semiconductor and into the depletion region under the bias voltage, thereby causing a change in the capacitance of the detector element;

c) a light source disposed to irradiate the gas with light before the gas enters the detector element at the inlet surface of the mesh electrode, the light source emits light at a wavelength corresponding to a molecular resonance of the chemical species and effective to enhance the adsorption selectivity of the organic semiconductor material with respect to the chemical species;

d) means for determining the presence of the chemical species in the gas based on the change in capacitance in the depletion region; and e) means for determining the concentration of the chemical species in the gas based on the change in capacitance in the depletion region.

13. The semiconductor chemical sensor of claim 12, further comprising means for drawing the gas into the detector element through the inlet surface of the mesh electrode.

14. The semiconductor chemical sensor of claim 12, wherein the intermediate layer comprises the organic semiconductor material on a porous insulating substrate.

15. The semiconductor chemical sensor of claim 12, wherein the organic semiconductor material comprises a heterocyclic compound.

16. The semiconductor chemical sensor of claim 12, wherein the organic semiconductor material comprises an aliphatic compound.

17. A portable semiconductor chemical sensor for determining the presence of a chemical species in a gas, the semiconductor chemical sensor comprising:

a) a support member sized to be held by a user;
b) a detector element on the support member, the detector element comprising:
i) an inlet surface; and
ii) a porous layer comprised of an organic semiconductor material on which the chemical species is adsorbed, the porous layer having a depletion region;

b) a power source electrically connected to the detector element to produce a bias voltage in the detector element such that the chemical species percolates through the porous layer and into the depletion region under the bias voltage, thereby changing the capacitance of the detector element;

c) a light source disposed to irradiate the gas with light before the gas enters the detector element at the inlet surface, the light source emits at least one light wavelength effective to change the chemical properties of the chemical species so as to enhance the adsorption selectivity of the organic semiconductor material with respect to the chemical species; and d) means for determining the presence of the chemical species in the gas based on the change in capacitance in the depletion region.

18. The portable semiconductor chemical sensor of claim 17, further comprising means for determining the concentration of the chemical species in the gas.

19. The portable semiconductor chemical sensor of claim 17, further comprising means positioned to draw the gas into the detector element through the inlet surface.

20. The portable semiconductor chemical sensor of claim 17, wherein the organic semiconductor material comprises a compound selected from the group consisting of heterocyclic compounds and aliphatic compounds.

21. A method of detecting a chemical species in a gas with a chemical sensor, comprising:

a) providing a detector element comprising:
i) an inlet surface; and
ii) a porous layer comprised of an organic semiconductor material on which the chemical species is adsorbed, the porous layer having a depletion region;

b) producing a bias voltage in the detector element such that the chemical species percolates through the organic 
semiconductor material and into the depletion region under the bias voltage, thereby changing the capacitance of the detector element;

c) irradiating the gas with light before the gas enters the detector element at the inlet surface of the mesh electrode, the light having a wavelength effective to enhance the adsorption selectivity of the organic semiconductor material with respect to the chemical species; and d) determining the presence of the chemical species in the gas based on the change in capacitance in the depletion region.

22. The method of claim 21, further comprising the step of determining the concentration of the chemical species in the gas based on the change in capacitance in the depletion region.

23. The method of claim 21, further comprising the step of drawing the gas into the detector element through the inlet surface.

24. The method of claim 21, wherein the light (i) decreases the concentration of the chemical species in the gas that can be detected by the chemical sensor, and (ii) for a given concentration of the chemical species in the gas, increases the capacitance change caused by percolation of the chemical species into the depletion region.

25. The method of claim 21, wherein the chemical species comprises cocaine and the organic semiconductor material comprises a phthalocyanine molecule.

* * * * *